(12) United States Patent
Elenko et al.

(10) Patent No.: US 10,272,155 B2
(45) Date of Patent: Apr. 30, 2019

(54) USE OF POLYMERIC MATERIALS WITH OTHER SUBSTANCES FOR IMPROVED PERFORMANCE

(71) Applicant: GELESIS, Inc., Boston, MA (US)

(72) Inventors: Eric Elenko, Boston, MA (US); Eyal S. Ron, Lexington, MA (US); Yishai Zohar, Boston, MA (US)

(73) Assignee: Gelesis LLC, Boston, MA (US)

( * ) Notice: Subject to any disclaimer, the term of this patent is extended or adjusted under 35 U.S.C. 154(b) by 0 days.

(21) Appl. No.: 14/597,600

(22) Filed: Jan. 15, 2015

(65) Prior Publication Data
US 2015/0196641 A1    Jul. 16, 2015

Related U.S. Application Data

(63) Continuation of application No. 12/403,788, filed on Mar. 13, 2009, now abandoned, which is a continuation of application No. 12/295,145, filed as application No. PCT/US2007/065351 on Mar. 28, 2007, now abandoned.

(60) Provisional application No. 60/786,615, filed on Mar. 28, 2006, provisional application No. 60/787,396, filed on Mar. 30, 2006.

(51) Int. Cl.
| A61K 47/22 | (2006.01) |
| A61K 9/00 | (2006.01) |
| A61K 31/785 | (2006.01) |

(52) U.S. Cl.
CPC .......... *A61K 47/22* (2013.01); *A61K 9/0065* (2013.01); *A61K 31/785* (2013.01)

(58) Field of Classification Search
None
See application file for complete search history.

(56) References Cited

U.S. PATENT DOCUMENTS

| 5,104,676 | A | | 4/1992 | Mahmoud et al. | |
| 5,543,405 | A | * | 8/1996 | Keown | A61K 31/28 514/161 |
| 6,271,278 | B1 | * | 8/2001 | Park | A61L 15/60 521/102 |
| 2004/0192582 | A1 | * | 9/2004 | Burnett | A61F 5/003 424/465 |

FOREIGN PATENT DOCUMENTS

| KR | 20050115017 A | 12/2005 |
| WO | 2004056393 A1 | 7/2004 |

OTHER PUBLICATIONS de la Torre et al. "Poly (acrylic acid) Chitosan Interpolymer Complexes for Stomach Controlled Antibiotic Delivery", Journal of Biomedical Materials Research Part B, 72B(1), 2005, pp. 191-197.*
Stùa-Birketvedt et al., "Cimetidine reduces weight and improves metabolic control in overweight patients with Type 2 diabetes", International Journal of Obesity, 1998 22, pp. 1041-1045. (Year: 1998).*

* cited by examiner

*Primary Examiner* — Melissa L Fisher
(74) *Attorney, Agent, or Firm* — Elmore Patent Law Group, P.C.; Edgar W. Harlan; Carolyn S. Elmore

(57) ABSTRACT

Methods of enabling or improving the ability of a hydrogel to swell in the stomach of an animal and/or increasing the amount of time said hydrogel remains swollen in the stomach are described herein. In one embodiment, a polymer is administered in combination with one or more pH modifying agents which raise and maintain the pH of the micro environment of the polymer and/or the stomach in order inducing swelling in the polymer. The polymer can be a homopolymer, a copolymer, or a polymer blend or composite. In one embodiment, the polymer is a superabsorbent polymer ("SAP"). The polymers can also be administered with one or more active agents, such as appetite suppressants. The pH modifying agent and/or the active agent can be administered simultaneously with the polymer in the same dosage form, simultaneously with the polymer in separate dosage forms, or sequentially. The compositions are formulated for oral administration. The formulation can include drugs for delivery to the stomach, such as antibiotics, or the hydrogel can be used as a filler, for example, for obesity control. The formulation an also be used to enhance gastric retention, for example, for controlled drug delivery. Methods of delivering a drug are also described herein, along with medicaments for carrying out the methods of the present invention.

12 Claims, No Drawings

USE OF POLYMERIC MATERIALS WITH OTHER SUBSTANCES FOR IMPROVED PERFORMANCE

RELATED APPLICATIONS

This application is a continuation application of U.S. application Ser. No. 12/403,788, filed Mar. 13, 2009, which is a continuation application of U.S. application Ser. No. 12/295,145, filed Mar. 28, 2007, (now abandoned) which is U.S. National stage entry of International Application No. PCT/US2007/065351, which designated the United States and was filed on Mar. 28, 2007, published in English, which claims the benefit of priority to U.S. Provisional Patent Application Ser. Nos. 60/786,615, filed Mar. 28, 2006, and 60/787,396, filed Mar. 30, 2006, both of which are hereby incorporated by reference in their entirety.

FIELD OF THE INVENTION

The present invention is in the field of methods for inducing weight loss and treatment of gastrointestinal disorders through mechanical and physiological means using polymers which are pH dependent by inducing the appropriate stomach pH and by further using the polymers in conjunction with other pharmacological and surgical means to induce weight loss.

BACKGROUND OF THE INVENTION

Public health efforts and current antiobesity agents have not controlled the increasing epidemic of obesity. This disorder is increasingly prevalent in industrialized nations because of the abundance of food and the reduced activity levels that accompany the movement of populations from rural to urban settings. Obesity is loosely defined as an excess of body fat over that needed to maintain health.

Obesity is associated with increased morbidity and mortality. Detrimental effects of obesity on health include an increased risk of cardiovascular disease and the associated conditions of hypertension, diabetes, and hyperlipidemia. Millions of people are clinically obese and, in view of the deleterious effects of obesity on health, would benefit from treatment. Additionally, many people, although not clinically obese, can improve their health and well-being by losing weight.

The pathogenesis of obesity is multifactorial and includes the control of feeding behavior, mechanisms of fat storage, the components of energy intake and expenditure, and genetic and psychological influences. Likewise, the treatment of obesity is generally multifactorial. Unfortunately, the mechanisms of fat storage and genetic influences are not, generally speaking, amenable to treatment. Moreover, the control of feeding behavior and psychological influences require prolonged treatment. In addition, although the components of energy intake and expenditure are treatable, many obese individuals are resistant to or incapable of engaging in activities which significantly increase their energy expenditure. Therefore, controlling energy intake is an attractive approach for the treatment of obesity.

Various drugs and drug classes are known to be weight loss and antiobesity agents. These drugs consist of biological path way affecting agents such as 1) central nervous system agents that affect neurotransmitters or neural ion channels; 2) leptin/insulin/central nervous system pathway agents; 3) gastrointestinal-neural pathway agents; 4) agents that may increase resting metabolic rate ("selective" β-3 stimulators/ agonist, uncoupling protein homologues, and thyroid receptor agonists); and 5) other more diverse agents. These suppressants, however, typically do not create a true feeling of satiation, such as that brought on by a "full" stomach and/or they cause undesirable side-effects, such as anxiety, and hyperactivity and may have adverse side effects.

Amphetamines (dextroamphetamine) have been used as weight loss and anti-obesity drugs, but can cause unacceptable tachycardia and hypertension. They also have a high rate of abuse potential. Other sympathomimetic adrenergic agents, including phentermine, benzphetamine, phendimetrazine, mazindol, and diethylpropion, may have adverse cardiovascular side effects, and their indicated use is only short-term (12 weeks), In 2000, the appetite suppressant phenylpropanolamine was removed from United States market because of unacceptable risks of stroke, especially in adult women. Other weight loss agents, such as orlistat and sibutramine, also can have adverse side effects. For example, orlistat use frequently results in adverse events including flatus, oily stools, fecal urgency or fecal incontinence, and abdominal pain, particularly among patients who do not follow the recommended low-fat diet. Further, daily multivitamin supplementation is recommended to prevent the potential of impaired absorption of fat-soluble vitamins (A, D, E, and K) that may theoretically occur with long-term use. The use of sibutramine may increase blood pressure and heart rate, and its use is contraindicated in patients with uncontrolled hypertension, CHD, cardiac dysrhythmias, congestive heart failure, or stroke.

The sensation of satiety as a means of suppressing of appetite is well known in the art and is linked to both obesity treatment and effecting weight loss. For example, U.S. Pat. No. 5,336,486 to Acharya et al. describes the false sensation of satiety induced by filling the stomach with heavy digestible vegetable fibers. Consuming large amounts of fiber, however, requires the patient to expel large quantities of fiber which can cause gastrointestinal discomfort. Others are unable tolerate such high volumes of fiber for other reasons. To diminish the discomfort caused by a full stomach which retains vegetable fibers for a period of time higher than is normal, diet recipes based on vegetable fibers have been refined by the addition of easily digestible products with a low number of calories. See U.S. Pat. No. 5,063,073 to Kratochvil; U.S. Pat. No. 5,654,028 to Christensen et al.; and U.S. Pat. No. 6,426,077 to Grace et al. U.S. Pat. Nos. 5,405,616 and 6,103,269 to Wounderlich et al. describe a material composed of gelatin or collagen hydrolysate, one or more active agents and one or more excipients (i.e., plasticizers, odorants, etc.). The material is prepared as a solution or suspension and then freeze-dried to obtain a solid material. The solid material can be administered as a powder, tablet or capsule. When the dried polymeric material comes in contact with the aqueous medium of the stomach, it first becomes swollen in a few minutes and then is dissolved, resulting in a solution that will not interfere with the emptying of the gastrointestinal tract.

Low caloric products for controlling body weight can be obtained by using collagenic biopolymers, such as: soluble collagen, gelatin or collagen hydrolysate. See U.S. Pat. Nos. 5,100,688; 5,211,976; 5,219,599; 5,665,234; 5,665,419. Commercial products, such as "Dietary Supplement—CALORAD®", produced by EYI—Essentially Yours Industries, Inc.—USA, have been used for weight loss control and also as a muscular stimulant, as well as an aid for osteoporosis and for arthritis treatment.

None of these drugs and materials, however, has provided a satisfactory means for control of obesity or to induce weight loss with adequate safety for the user.

Absorbent materials for water and aqueous media, including fluids secreted by the human body, are well known in the literature. These materials are typically polymer-based and are produced in the form of powders, granules, microparticles or fibers. Upon contact with an aqueous medium, these polymeric materials swell by absorbing the liquid phase into their structure without dissolving. A "hydrogel" is a polymeric material which has the ability to absorb water and swell. If the water absorbency is more than 20 g water per 1 g of dried polymer, the material is referred to as a "superabsorbent polymer" (SAP). The swelling of these materials in the stomach can cause a sensation of satiety (i.e., full stomach). The sensation of satiety as a means of suppressing appetite is well known in the art and has been used to treat obesity and/or induce weight loss.

Polymeric hydrogels have also been used for controlled drug delivery, particularly for extended release and/or delayed release formulations. In pharmaceutical applications, the drug is typically dispersed within the polymeric material. The rate of release of the drug is dependent on the rate of diffusion of the drug from the hydrogel and/or the rate of degradation of the polymer material. The oral administration of drugs generally uses one of two classes of hydrogels a) those which release drug in the stomach and b) those which release drug in the small intestine or other locations such as the oral cavity, duodenum, etc. The use of hydrogels for the controlled release of active agents, using the "full stomach" principle, has been described in U.S. Pat. No. 3,574,820 to Johnson et al.; U.S. Pat. No. 4,264,493 to Battista; U.S. Pat. No. 4,758,436 to Caldwell et al.; U.S. Pat. No. 5,614,223 to Sipos; U.S. Pat. No. 6,319,510 to Yates; U.S. Pat. No. 6,476,006 to Flashner-Barak et al.; and U.S. Pat. No. 6,485,710 to Zuckerman.

The stomach produces a gastric secretion that is an aqueous medium containing water, hydrochloric acid, pepsin and mucus (polysaccharide biogel). This medium has a pH of 1-3 and contains pepsin proteolytic enzyme. The small intestine secretes an aqueous medium with a chemical composition more complex than that of the stomach. It is characterized by pH of 5-9 and displays biodegradative enzymatic activity in both proteins and polysaccharides. Hydrogels, which are designed to function in the stomach, must be able to (1) swell in acid aqueous media and maintain its volume for a sufficient amount of time to induce therapeutically relevant effects; and (2) be easily eliminated once its function has been fulfilled, to avoid obstruction of the intestinal or gastric tract and to avoid the generation of toxic byproducts.

Unfortunately, many hydrogels that could be used for therapeutic purposes including weight loss and obesity treatment do not swell or swell poorly in the acidic pH of the stomach. Park et al. demonstrated that the swelling ratio of the poly(acrylamide-co-acrylic acid) was dependent on the pH of the medium. At a pH of around 5 the hydrogel showed maximum swelling. The poly(acrylamide-co-acrylic acid) showed repeated swelling and shrinking by alternating the medium pH between 1.2 and 7.5, and the changes in swelling ratio was quite fast occurring in a matter of minutes (Park et al., J Biomater Sci Polym Ed., 11(12), 1371-80 (2000)). Peppas et al. describe copolymers of methacrylic acid (MAA) and 2-methacryloxyethy 1 glucoside (MEG), have pH dependent swelling, with a transition between the swollen and the collapsed states occurred at a pH of 5. The swelling ratios of the hydrogels increased at pH values above 5 (Peppas et al., J. Biomater. Sci. Polymer Edn, Vol. 13, No. 1, pp. 1271-1281 (2002)).

U.S. Pat. No. 5,876,741 to Ron et al describes hydroxypropyl cellulose (HPC) hydrogels crosslinked with adipic acid exhibiting a swelling curve with minimal response at pH<5.0 and a significant response for pH>5.0. This HPC hydrogel crosslinked with adipic acid exhibited nearly ideal results with zero water absorbance at pH<5.0, moderate swelling for 5<pH<7 and over 20 fold swelling for pH>7.

There exists a need for methods to induce swelling of polymeric hydrogels in the low acidity of the stomach for the treatment of obesity and other gastric disorders.

It is therefore an object of the present invention to provide methods to induce satiation and reduce appetite utilizing mechanical and physiological means for the treatment of obesity and other gastric disorders.

SUMMARY OF THE INVENTION

In one aspect, the present invention relates to a method of enabling or improving the ability of a hydrogel to swell in the stomach of an animal and/or increasing the amount of time said hydrogel remains swollen in the stomach comprising administering to the animal a water-swellable polymer in combination with one or more substances which raise and maintain the pH of the microenvironment of the polymer and/or the stomach. In a further embodiment, the polymer is a superabsorbent polymer. In a further embodiment, the polymer is selected from the group consisting of homopolymers, copolymers, polymer blends, cross-linked polymers, polymer composites, and combinations thereof. In a further embodiment, the polymer is a polymer composite.

In a further embodiment, the one or more substances which alter the pH are selected from the group consisting of buffers, $H_2$ blockers, proton pump inhibitors, antacids, proteins, nutritional shakes, and combinations thereof. In a further embodiment, the buffer is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, sodium carbonate, sodium hydroxide, and combinations thereof. In a further embodiment, the $H_2$ blocker is selected from the group consisting of cimetidine, ranitidine, famotidine, nizatidine, and combinations hereof. In a further embodiment, the proton pump inhibitor is selected from the group consisting of omeprazole, lansoprazole, esomeprazole, pantoprazole, abeprazole, and combinations thereof. In a further embodiment, the antacid is selected from the group consisting of aluminum hydroxide, magnesium hydroxide, aluminum carbonate, calcium carbonate, and hydrotalcite.

In a further embodiment, the polymer further comprises one or more pharmaceutically acceptable excipients selected from the group consisting of plasticizers, diluents, binders, lubricants, colorants, stabilizers, surfactants, flavorants, preservatives, anti-oxidants, buffering agents and combinations thereof. In a further embodiment, the buffering agent is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, odium carbonate, sodium hydroxide, and combinations thereof.

In a further embodiment, the polymer is administered with one or more therapeutically active, diagnostic or prophylactically active agents. In a further embodiment, the agent is selected from the group consisting of analgesics, anti-inflammatory drugs, antipyretics, antidepressants, altiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, appetite suppressants, antiobesity agent, anti-narcoleptics, and combinations thereof. In a further embodiment, the agent is an appetite suppressant or antiobesity agent. In a further embodiment, the appetite suppressant or antiobesity agent is selected from the group consisting of sibutramine hydrochloride, orlistat, rimonabant, benzphetamine, diethylpropion, mazindol phendimetrazine, phentermine, amphetamine, fenfluramine, nalmetrene, and combinations thereof.

In a further embodiment, the polymer is formulated for oral administration. In a further embodiment, the formulation is selected from the group consisting of tablets, capsules, syrups, solutions, suspensions, powders, bars and shakes.

In a further embodiment, the substance which raises the pH of the microenvironment of the polymer and/or the stomach is administered simultaneously with the polymer in the same dosage form. In a further embodiment, the substance which raises the pH of the microenvironment of the polymer and/or the stomach is administered simultaneously with the polymer in different dosage forms. In a further embodiment, the substance which raises the pH of the microenvironment of the polymer and/or the stomach is administered before or after administration of the polymer. In a further embodiment, the substance which raises the pH of the microenvironment of the polymer and/or the stomach is administered within 24 hours of administration of the polymer. In a further embodiment, the substance which raises the pH of the microenvironment of the polymer and/or the stomach is administered within 2 hours of administration of the polymer. In a further embodiment, the substance which raises the pH of the microenvironment of the polymer and/or the stomach is administered within 6 hours of administration of the polymer.

In a further embodiment, the methods of the present invention further comprise administering a substance which causes the hydrogel to degrade, disperse, and/or shrink after the hydrogel has resided in the stomach for a time. In a further embodiment, the substance is administered after the administration of the polymer. In a further embodiment, the substance acts to lower the pH of the microenvironment of the polymer and/or the stomach. In a further embodiment, the substance is an organic acid. In a further embodiment, the substance is an acidic drink, such as orange juice or Coca Cola. In a further embodiment, the substance is a protein. In a further embodiment, the protein is an enzyme. In a further embodiment, the enzyme is selected from the group consisting of pepsin, pancreatin, and combinations thereof.

In a further embodiment, the polymer and substance are administered in conjunction with a surgical intervention for obesity. In a further embodiment, the surgical intervention to treat obesity is selected from the group consisting of gastric banding, gastric bypass surgery, intragastric balloon, implantable gastric stimulator and gastric electrical stimulation.

In a further embodiment, the water-swellable formulation is in the form of a shake, optionally including vitamins, mineral, or nutraceuticals, which is effective to increase stomach pH to enhance swelling of the polymer, to supplement dietary nutrients, or induce satiation and weight loss.

In a further embodiment, the animal is a primate, bovine, ovine, equine, porcine, avian, rodent, feline, or canine. In a further embodiment, the animal is a human.

In another aspect, the present invention relates to a method of delivering a drug to an animal comprising administering to the animal a water-swellable polymer comprising the drug, and one or more substances which raises the pH of the microenvironment of the polymer and/or stomach of the animal. In a further embodiment, the drug is released from the polymer in a sustained manner. In a further embodiment, the drug is selected from the group consisting of a therapeutically active, diagnostic, and prophylactically active agent. In a further embodiment, the agent is selected from the group consisting of analgesics, anti-inflammatory drugs, antipyretics, antidepressants, altiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, appetite suppressants, antiobesity agent, anti-narcoleptics, and combinations thereof. In a further embodiment, the agent is an appetite suppressant or antiobesity ant is selected from the group consisting of sibutramine hydrochloride, orlistat, rimonabant, benzphetamine, diethylpropion, mazindol phendimetrazine, phentermine, amphetamine, fenfluramine, nalmetrene, and combinations thereof.

In another aspect, the present invention relates to a method of delivering a drug to an animal comprising administering to the animal a water-swellable polymer comprising the drug, and one or more substances which raises the pH of the microenvironment of the polymer and/or stomach of the animal. In a further embodiment, the drug is released from the polymer in a sustained manner. In a further embodiment, the drug is selected from the group consisting of a therapeutically active, diagnostic, and prophylactically active agent. In a further embodiment, the agent is selected from the group consisting of analgesics, anti-inflammatory drugs, antipyretics, antidepressants, altiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, appetite suppressants, antiobesity agent, anti-narcoleptics, and combinations thereof. In a further embodiment, the agent is an appetite suppressant or antiobesity agent. In a further embodiment, the appetite suppressant or antiobesity agent is selected from the group consisting of sibutramine hydrochloride, orlistat, rimonabant, benzphetamine, diethylpropion, mazindol phendimetrazine, phentermine, amphetamine, fenfluramine, nalmetrene, and combinations thereof.

In a further embodiment, the polymer is a superabsorbent polymer. In a further embodiment, the polymer is selected from the group consisting of homopolymers, copolymers, polymer blends, cross-linked polymers, polymer composites, and combinations thereof. In a further embodiment, the polymer is a polymer composite.

In a further embodiment, the one or more substances which alter the pH are selected from the group consisting of buffers, $H_2$ blockers, proton pump inhibitors, antacids, proteins, nutritional shakes, and combinations thereof. In a further embodiment, the buffer is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, sodium carbonate, sodium hydroxide, and combinations thereof. In a further embodiment, the $H_2$ blocker is selected from the group consisting of cimetidine, ranitidine, famotidine, nizatidine, and combinations hereof. In a further embodiment, the proton pump inhibitor is selected from the group consisting of omeprazole, lansoprazole, esomeprazole, pantoprazole, abeprazole, and combinations thereof. In a further embodiment, the antacid is selected from the group consisting of aluminum hydroxide, magnesium hydroxide, aluminum carbonate, calcium carbonate, and hydrotalcite.

In a further embodiment, the polymer further comprises one or more pharmaceutically acceptable excipients selected from the group consisting of plasticizers, diluents, binders, lubricants, colorants, stabilizers, surfactants, flavorants, preservatives, anti-oxidants, buffering agents and combinations thereof. In a further embodiment, the buffering agent is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, odium carbonate, sodium hydroxide, and combinations thereof.

In a further embodiment, the polymer is formulated for oral administration. In a further embodiment, the formulation is selected from the group consisting of tablets, capsules, syrups, solutions, suspensions, powders, bars and shakes.

In a further embodiment, the substance which raises the pH of the microenvironment of the polymer and/or the stomach is administered simultaneously with the polymer in the same dosage form. In a further embodiment, the substance which raises the pH of the microenvironment of the polymer and/or the stomach is administered simultaneously with the polymer in different dosage forms. In a further embodiment, the substance which raises the pH of the microenvironment of the polymer and/or the stomach is administered before or after administration of the polymer. In a further embodiment, the substance which raises the pH of the microenvironment of the polymer and/or the stomach is administered within 24 hours of administration of the polymer. In a further embodiment, the substance which raises the pH of the microenvironment of the polymer and/or the stomach is administered within 2 hours of administration of the polymer. In a further embodiment, the substance which raises the pH of the microenvironment of the polymer and/or the stomach is administered within 6 hours of administration of the polymer.

In a further embodiment, the methods of the present invention further comprise administering a substance which causes the hydrogel to degrade, disperse, and/or shrink after the hydrogel has resided in the stomach for a time. In a further embodiment, the substance is administered after the administration of the polymer. In a further embodiment, the substance acts to lower the pH of the microenvironment of the polymer and/or the stomach. In a further embodiment, the substance is an organic acid. In a further embodiment, the substance is an acidic drink, such as orange juice or Coca Cola. In a further embodiment, the substance is a protein. In a further embodiment, the protein is an enzyme. In a further embodiment, the enzyme is selected from the group consisting of pepsin, pancreatin, and combinations thereof.

In a further embodiment, the polymer and substance are administered in conjunction with a surgical intervention for obesity. In a further embodiment, the surgical intervention to treat obesity is selected from the group consisting of gastric banding, gastric bypass surgery, intragastric balloon, implantable gastric stimulator and gastric electrical stimulation.

In a further embodiment, the water-swellable formulation is in the form of a shake, optionally including vitamins, mineral, or nutraceuticals, which is effective to increase stomach pH to enhance swelling of the polymer, to supplement dietary nutrients, or induce satiation and weight loss.

In a further embodiment, the animal is a primate, bovine, ovine, equine, porcine, avian, rodent, feline, or canine. In a further embodiment, the animal is a human.

In a further embodiment, the methods of the present invention are to treat obesity, induce weight loss, and/or increase gastric retention.

In another aspect, the present invention relates to a medicament for enabling or improving the ability of a hydrogel to swell in the stomach of an animal and/or to increase the amount of time said hydrogel remains swollen in the stomach comprising a water-swellable polymer in combination with one or more substances which raise and maintain the pH of the microenvironment of the polymer and/or the stomach. In a further embodiment, the polymer is a superabsorbent polymer. In a further embodiment, the polymer is selected from the group consisting of homopolymers, copolymers, polymer blends, polymer composites, and combinations thereof. In a further embodiment, the polymer is a polymer composite.

In a further embodiment, the one or more substances which alter the pH are selected from the group consisting of buffers, $H_2$ blockers, proton pump inhibitors, antacids, proteins, nutritional shakes, and combinations thereof. In a further embodiment, the buffer is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, sodium carbonate, sodium hydroxide, and combinations thereof. In a further embodiment, the $H_2$ blocker is selected from the group consisting of cimetidine, ranitidine, famotidine, nizatidine, and combinations hereof. In a further embodiment, the proton pump inhibitor is selected from the group consisting of omeprazole, lansoprazole, esomeprazole, pantoprazole, abeprazole, and combinations thereof. In a further embodiment, the antacid is selected from the group consisting of aluminum hydroxide, magnesium hydroxide, aluminum carbonate, calcium carbonate, and hydrotalcite.

In a further embodiment, the medicament further comprises one or more pharmaceutically acceptable excipients selected from the group consisting of plasticizers, diluents, binders, lubricants, colorants, stabilizers, surfactants, flavorants, preservatives, anti-oxidants, buffering agents and combinations thereof. In a further embodiment, the buffering agent is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, odium carbonate, sodium hydroxide, and combinations thereof.

In a further embodiment, the medicament further comprises one or more therapeutically active, diagnostic or prophylactically active agents. In a further embodiment, the agent is selected from the group consisting of analgesics, anti-inflammatory drugs, antipyretics, antidepressants, altiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, appetite suppressants, antiobesity agent, anti-narcoleptics, and combinations thereof. In a further embodiment, the agent is an appetite suppressant or antiobesity agent. In a further embodiment, the appetite suppressant or antiobesity agent is selected from the group consisting of sibutramine hydrochloride, orlistat, rimonabant, benzphetamine, diethylpropion, mazindol phendimetrazine, phentermine, amphetamine, fenfluramine, nalmetrene, and combinations thereof.

In a further embodiment, the medicament is formulated for oral administration. In a further embodiment, the formulation is selected from the group consisting of tablets, capsules, syrups, solutions, suspensions, powders, bars and shakes.

In a further embodiment, the substance which raises the pH of the microenvironment of the polymer and/or the stomach and the polymer are in the same dosage form. In a further embodiment, the substance which raises the pH of the microenvironment of the polymer and/or the stomach and the polymer are in different dosage forms.

In a further embodiment, the medicaments of the present invention further comprise a substance which causes the polymer to degrade, disperse, and/or shrink after the polymer has resided in the stomach for a time. In a further embodiment, the substance acts to lower the pH of the microenvironment or the polymer and/or the stomach. In a further embodiment, the substance is an organic acid. In a further embodiment, the substance is an acidic drink, such as orange juice or COCA-COLA®. In a further embodiment, the substance is a protein.

In a further embodiment, the medicament is in the form of a shake, optionally including vitamins, mineral, or nutraceuticals, which is effective to increase stomach pH to enhance swelling of the polymer, to supplement dietary nutrients, or induce satiation and weight loss.

In another aspect, the present invention relates to a medicament for delivering a drug to an animal comprising a water-swellable polymer comprising the drug, and one or more substances which raises the pH of the microenvironment of the polymer and/or stomach of the animal. In a further embodiment, the drug is released from the polymer in a sustained manner. In a further embodiment, the drug is selected from the group consisting of a therapeutically active, diagnostic, and prophylactically active agent. In a further embodiment, the agent is selected from the group consisting of analgesics, anti-inflammatory drugs, antipyretics, antidepressants, altiepileptics, antihistamines, antimigraine drugs, antimuscarinics, anxioltyics, sedatives, hypnotics, antipsychotics, bronchodilators, anti asthma drugs, cardiovascular drugs, corticosteroids, dopaminergics, electrolytes, gastro-intestinal drugs, muscle relaxants, nutritional agents, vitamins, parasympathomimetics, stimulants, anorectics, appetite suppressants, antiobesity agent, anti-narcoleptics, and combinations thereof. In a further embodiment, the agent is an appetite suppressant or antiobesity agent. In a further embodiment, the appetite suppressant or antiobesity agent is selected from the group consisting of sibutramine hydrochloride, orlistat, rimonabant, benzphetamine, diethylpropion, mazindol phendimetrazine, phentermine, amphetamine, fenfluramine, nalmetrene, and combinations thereof.

In a further embodiment, the polymer is a superabsorbent polymer. In a further embodiment, the polymer is selected from the group consisting of homopolymers, copolymers, polymer blends, cross-linked polymers, polymer composites, and combinations thereof. In a further embodiment, the polymer is a polymer composite.

In a further embodiment, the one or more substances which alter the pH are selected from the group consisting of buffers, $H_2$ blockers, proton pump inhibitors, antacids, proteins, nutritional shakes, and combinations thereof. In a further embodiment, the buffer is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, sodium carbonate, sodium hydroxide, and combinations thereof. In a further embodiment, the $H_2$ blocker is selected from the group consisting of cimetidine, ranitidine, famotidine, nizatidine, and combinations hereof. In a further embodiment, the proton pump inhibitor is selected from the group consisting of omeprazole, lansoprazole, esomeprazole, pantoprazole, abeprazole, and combinations thereof. In a further embodiment, the antacid is selected from the group consisting of aluminum hydroxide, magnesium hydroxide, aluminum carbonate, calcium carbonate, and hydrotalcite.

In a further embodiment, the polymer further comprises one or more pharmaceutically acceptable excipients selected from the group consisting of plasticizers, diluents, binders, lubricants, colorants, stabilizers, surfactants, flavorants, preservatives, anti-oxidants, buffering agents and combinations thereof. In a further embodiment, the buffering agent is selected from the group consisting of ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, odium carbonate, sodium hydroxide, and combinations thereof.

In a further embodiment, the polymer is formulated for oral administration. In a further embodiment, the formulation is selected from the group consisting of tablets, capsules, syrups, solutions, suspensions, powders, bars and shakes.

In a further embodiment, the substance which raises the pH of the microenvironment of the polymer and/or the stomach is administered simultaneously with the polymer in the same dosage form. In a further embodiment, the substance which raises the pH of the microenvironment of the polymer and/or the stomach is administered simultaneously with the polymer in different dosage forms. In a further embodiment, the substance which raises the pH of the microenvironment of the polymer and/or the stomach is administered before or after administration of the polymer. In a further embodiment, the substance which raises the pH of the microenvironment of the polymer and/or the stomach is administered within 24 hours of administration of the polymer. In a further embodiment, the substance which raises the pH of the microenvironment of the polymer and/or the stomach is administered within 2 hours of administration of the polymer. In a further embodiment, the substance which raises the pH of the microenvironment of the polymer and/or the stomach is administered within 6 hours of administration of the polymer.

In a further embodiment, the medicaments of the present invention further comprise a substance which causes the hydrogel to degrade, disperse, and/or shrink after the hydrogel has resided in the stomach for a time. In a further embodiment, the substance is administered after the administration of the polymer. In a further embodiment, the substance acts to lower the pH of the microenvironment of the polymer and/or the stomach. In a further embodiment, the substance is an organic acid. In a further embodiment, the substance is an acidic drink, such as orange juice or COCA-COLA®. In a further embodiment, the substance is a protein. In a further embodiment, the protein is an enzyme. In a further embodiment, the enzyme is selected from the group consisting of pepsin, pancreatin, and combinations thereof.

In a further embodiment, the medicament is administered in conjunction with a surgical intervention for obesity. In a further embodiment, the surgical intervention to treat obesity is selected from the group consisting of gastric banding, gastric bypass surgery, intragastric balloon, implantable gastric stimulator and gastric electrical stimulation.

In a further embodiment, the water-swellable formulation is in the form of a shake, optionally including vitamins, mineral, or nutraceuticals, which is effective to increase stomach pH to enhance swelling of the polymer, to supplement dietary nutrients, or induce satiation and weight loss.

In a further embodiment, the animal is a primate, bovine, ovine, equine, porcine, avian, rodent, feline, or canine. In a further embodiment, the animal is a human.

These embodiments of the present invention, other embodiments, and their features and characteristics, will be apparent from the description and claims that follow.

DETAILED DESCRIPTION OF THE INVENTION

I. Definitions

The term "polymer composite" as used herein, refers to a macromolecular material composed of two or more polymer chains, wherein the polymer chains interact via non-covalent interactions such as Van der Waals forces, hydrogen bondings, ionic interactions, etc. The composite has a macromolecular configuration of a three-dimensional network type stabilized by multiple bond types.

The term "polymer blend" as used herein, refers to a macroscopically homogeneous mixture of two or more different species of polymer.

II. Hydrogels and Methods of Enabling and/or Improving Hydrogel Swelling

Methods of enabling and/or improving hydrogel swelling in the stomach of an animal or human by administering a composition containing a polymer in combinations with one or more pH modifying agents which raise and maintain the pH of the microenvironment of the polymer and/or the stomach and increasing the time the polymer remains swollen in the stomach are described herein.

A. Polymers

The polymer can be a homopolymer, a copolymer, a cross-linked polymer, a polymer blend or polymer composite. In one embodiment, the polymer is a superabsorbent polymer. Suitable polymers which form can form a hydrogel include, but are not limited to, synthetic or natural polymers. Examples of synthetic polymers include polyacrylic and polymethacrylic acid polymers, cellulose derivatives such as hydroxypropyl cellulose, polyethyleneglycol polymers, copolymers and block copolymers, and other water swellable, biocompatible polymers. Examples of natural polymers include collagen, hyaluronic acid, gelatin, albumin, polysaccharide, and derivatives thereof. Natural polymers can also be of the type isolated from various plant materials such as psyllium.

Structurally, the water-absorbent polymeric materials are three-dimensional macromolecular configurations. They are produced through several methods: a) synthesis from monomers (cross-linking polymerization); b) synthesis from polymers and polymerization auxiliary (grafting and crosslinking polymerization); c) synthesis from polymers and non-polymerization auxiliary (cross-linking polymers); d) synthesis from polymers with energy sources (cross-linking polymers without auxiliaries) and e) synthesis from polymers (cross-linking by reactive polymer-polymer intercoupling). The raw materials and technology used in synthesis are main factors in the creation of hydrogels' key properties and their range of applications.

There are a known number of methods for obtaining high purity absorbent materials for aqueous media with three-dimensional polymeric configurations and with potential applications in pharmaceutical and/or medical field: a) chemical methods: ionic and/or coordinative intercomplexing (i.e., U.S. Pat. No. 4,570,629 to Widra and U.S. Pat. No. 5,153,174 to Band et al.); cross-linking with oligomers or reactive polymers that have reactive groups with double bonds or rings (i.e., U.S. Pat. No. 5,489,261 Franzblau et al and U.S. Pat. No. 5,863,984 to Doillon et at.); cross-linking with radiation (i.e., U.S. Pat. No. RE33,997 to Kuamz et al.; U.S. Pat. No. 4,264,155 to Miyata; and U.S. Pat. No. 5,948,429 to Bell et al.); and b) physical methods: cross-linking with microwaves (i.e., U.S. Pat. Nos. 5,859,077 and 6,168,762 to Reichman et al.); freeze-drying (i.e., U.S. Pat. No. 5,676,967 to Williams et al. and U.S. Pat. No. 5,869,080 to McGregor et al); and dehydrothermo-crosslinking (i.e., U.S. Pat. No. 4,837,285 to Berg et al; U.S. Pat. No. 4,950,485 to Akhtar et al.; and U.S. Pat. No. 4,971,954 to Brodsky et al.).

Dehydrothermo-crosslinking, as with the other physical methods for obtaining three-dimensional structures, eliminates the risk of toxic effects that can be produced by secondary products of the reaction or energy state modification of the reaction product (in which appear new types of covalent, ionic or coordinative bonds), which can occur in the activation of some chemical processes. Moreover, compared with freeze-drying or cross-linking via microwaves, dehydrothermo-crosslinking offers many more possibilities to regulate the structural characteristics of the resulting three-dimensional networks (i.e., Scotchford C. A., Cascone G. D., Ownes S., Gusti P., "Osteoblast responses of collagen-PVA bioartificial polymers in vitro: the effects of cross-linking method and collagen content", Biomaterials 19, 1-11, 1998; Giunchedi P., Genta I., Conti B., Muzzarelli R. A. A., Conti B., Biomaterials 19,157-161, 1998). The hydrogels based on collagenic biopolymers obtained by dehydrothermo-crosslinking, however, do not have high absorption capacities.

B. pH Modifying Agents

The polymeric material can be co-administered with one or more pH modifying agents to raise and maintain the pH of the microenvironment of the polymer and/or the stomach. Suitable pH modifying agents include buffers, proton pump inhibitors, $H_2$ blocker, and antacids. Example of these pH modifying agents are described below. The compositions can act as stomach filling materials which, upon hydration, swell and generate a sensation of satiety. The pH modifying agent can be administered simultaneously with the polymer in the same dosage form, simultaneously with the polymer is separate dosage forms or sequentially. If the pH modifying agent in administered sequentially with the polymer composition, than the pH modifying agent is preferably administered within 24 hours, more preferably with 12 hours, and most preferably within 6 hours of administration of the polymer composition.

i Buffers

Suitable pH buffers include, but are not limited to, ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, sodium carbonate, sodium hydroxide, and combinations thereof.

ii Proton Pump Inhibitors

Suitable proton pump inhibitors include, but are not limited to, omeprazole (LOSEC®, PRILOSEC®), omeprazole in combinations with bicarbonate (ZEGERID®, RAPINEX®), lansoprazole (PREVACID®, ZOTON®), esomeprazole (NEXIUM®), pantoprazole (PROTONIX®, SOMAC®, PANTOLOC®), and rabeprazole (ACIPHEX®, PARIET®).

iii $H_2$ Blockers

Suitable $H_2$ blockers include, but are not limited to, cimetidine (TAGAMET®), ranitidine (ZANTAC®), famotidine (PEPCID®), famotidine in combination with calcium carbonate and magnesium hydroxide (PEPCID® complete), and nizatidine (AXID®, TAZAC®).

iv Antacids

Suitable over-the-counter antacids include, but are not limited to, aluminum hydroxide (AMPHOJEL®, ALTERNAGEL®), magnesium hydroxide (MILK OF MAGNESIA®), aluminum hydroxide in combination with magnesium hydroxide (MAALOX®, MYLANTA®), aluminum carbonate gel (BASAJEL®), calcium carbonate (TUMS®, TITRALAC®, calcium rich ROLAIDS®), and hydrotalcite (TALCID®).

C. Active Agents

The compositions can also be used for the controlled delivery of one or more therapeutically active, diagnostic, or prophylactic agents. The release rate of the active agent is dependent on the rate of diffusion of the active agent from the hydrogel as well as the rate of degradation of the polymeric composite.

Exemplary agents include analgesics, anti-inflammatory agents, antihelmintics, anti-arrhythmic agents, anti-bacterial agents, anti-viral agents, anti-hypertensive agents, anti-coagulants, anti-depressants, anti-diabetics, anti-epileptics, anti-fungal agents, anti-gout agents, anti-malarials, anti-migraine agents, anti-muscarinic agents, anti-neoplastic agents, erectile dysfunction improvement agents, immunosupressants, anti-protozoal agents, anti-thyroid agents, anxiolytic agents, sedatives, hypnotics, neuroleptics, -blockers, cardiac inotropic agents, corticosteroids, diuretics, anti-parkinsonian agents, gastro-intestinal agents, histamine $H_1$ and $H_2$ receptor antagonists, keratolytics, lipid regulating agents, anti-anginal agents, nutritional agents, opioid analgesics, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, non essential fatty acids, vitamins, minerals, appetite suppressants and mixtures thereof.

In one embodiment, the polymer composition is administered in combination with an appetite suppressant. The appetite suppressant can be administered before or after administration of the polymer composition. Alternatively, the appetite suppressant can be administered simultaneously with the polymer composition. Suitable appetite suppressants include, but are not limited to, MERIDIA® (sibutramine hydrochloride available from Abbott Laboratories), XENICAL® (orlistat available from Roche USA), ACOMPLIA® (Rimonabant, developed by Sanofi-Aventis and awaiting FDA approval), rimonabant, benzphetamine, diethylpropion, mazindol phendimetrazine, phentermine, amphetamine, fenfluramine, nalmetrene, and combinations thereof. The polymer composition can also be administered in combination with surgical treatments to treat obesity such as gastric banding, gastric bypass surgery, intragastric balloon, implantable gastric stimulator (awaiting U.S. approval) and gastric electrical stimulation (awaiting U.S. approval).

D. Other Excipients

The polymeric composites described herein can be formulated with one or more pharmaceutically acceptable excipients to treat a variety of gastrointestinal disorders as well as to provide controlled release of one or more active agents. Suitable excipients include pH modifying agents, plasticizers, colorants, flavorants, preservatives, anti-oxidants, surfactants, dispering agents, glidants, diluents, binding agents, and combinations thereof.

E. Nutritional Shakes

Shakes include any drink containing food additives. Food additives include, but are not limited to, flavorings, vitamins, minerals, and buffers. In one embodiment, the polymer composition is administered as a shake or in conjunction with a shake, which is consumed by the patient. A shake containing vitamins, minerals, optionally nutraceuticals, can serve the purpose of supplying nutrients which the patient might otherwise not ingest due to reduced meal size. The shake can contain one or more proteins which are co-administered with the polymer composition. It is well known in the art that proteins can raise and maintain the pH of the stomach. The shake can contain buffers which raise the pH of the stomach, allowing the polymer to swell and exert a therapeutic effect. Such buffers may include, but are not limited to, ammonium bicarbonate, ammonium carbonate, ammonium hydroxide, sodium bicarbonate, calcium carbonate, calcium hydroxide, magnesium carbonate, potassium bicarbonate, potassium carbonate, potassium hydroxide, sodium carbonate, sodium hydroxide, and combinations thereof. The shake can contain any combination of vitamins, minerals and buffers. A number of shakes are known to induce satiety, leading to weight loss (e.g., SLIM-FAST®). The polymer can be used in combination with the shake to have an advantageous effect in promoting satiety. The polymer may be taken in combination with commercially available shakes to raise stomach pH and/or supply required nutrients patients lack due to reduced meal size and/or produce an enhanced effect on satiety. Commercially available shakes, include, but are not limited to, SLIM-FAST®, GOLEAN® Protein Meal Chocolate Shake, Optimum Nutrition Complete Protein Diet Meal Shake Mix, WALKER DIET® Low Carb Shake, WALKER DIET® Fiber Combinations, Diet Lean Low Carb Shakes, NATURADE® Diet Lean—Low Carb Dieter's Shake, DIET SHAKE VANILLA ATKINS® NUTRITIONALS, OXESLIM® Diet Shake 2 Go, Protein Drink Mix by HERBALIFE®, Formula 1 Nutritional Shake Mix by HERBALIFE®, BASIC ORGANICS®, PAT'S DIET SHAKE®, UNIVERSAL NUTRITION® Specialized Protein for Dieting, Meal Replacement Protein Shake by SPORTPHARMA®, Whey Protein Shake by SPORTPHARMA®, MEDIFAST® Ready-to-Drink Shakes, EATING FOR LIFE® Right! for Women Nutrition Shake, Chocolate, GENISOY® Soy Protein Powder Natural, ATKINS® Rtd Shake, MUSCLETECH® NITRO-TECH® RTDs, KETOSLIM® Shake, GENISOY® Soy Protein Shake, SPIRU-TEIN® Sport, SPIRU-TEIN®, EAS® MYOPLEX® Lite, Protein Diet by Optimum, POWER SHAKE®, NUTRIMELT® Meal Replacement Protein Shake, NRG® Protein Booster, NATURE'S PLUS® KETO-SLIM® Shake, TODIETFOR® shakes, NUTRITECH® All One Powder, TOTAL SOY® French Vanilla, TOTAL BALANCE® Drink Mix, PRO V60® Straw, Slim & Trim Vanilla Cream, SCITEC NUTRITION® Protein Delite, METRX® Meal Replacement, ENSURE® High Protein Complete Balanced Nutrition Drink.

III. Methods of Administering

The polymer compositions are typically administered orally. Suitable oral dosage forms include tablets, capsules, caplets, powders, syrups, solutions, suspension and shakes. In one embodiment, the polymer compositions is compressed with one or more excipients and optionally with one or more pH modifying agents, and/or one or more active agents to form a tablet. Suitable excipients used to prepare tablets include binding agents, preservatives, antioxidants, glidants, flavorants, colorants, and combinations thereof.

In one embodiment, the polymer is encapsulated in a hard or soft gelatin capsule. The capsule fill material contains the polymer, and optionally one or more pH modifying agents and/or active agents. The fill material may also contain one or more excipients. Suitable excipients include, but are not limited to, plasticizers, crystallization inhibitors, wetting agents, bulk filling agents, solubilizers, bioavailability enhancers, solvents, and combinations thereof. Once the hydrogel has resided in the stomach for an appropriate amount of time (to suppress appetite and/or release one or more active agents), the polymer composition can be degraded, dispersed, or eroded to alleviate the sensation of satiety and/or avoid discomfort and/or harm to the patient. In one embodiment, a substance which increases the acidity of the microenvironment of the polymer and/or the stomach is administered to cause the polymer to shrink (by lowering the pH). Suitable substances include, but are not limited to, organic acids such as citric acid and phosphonic acid salts. For polymers which are composed partially of protein, enzymes such as pepsin or pancreatin are suitable substances.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

IV. In Vivo Testing

Laboratory rats were given a polymeric material of the present invention, PMSF-1, by oral gavage under different experimental conditions (see Example 1 in the Exemplification section). PMSF-1 was prepared in accordance with the procedures presented in U.S. Pat. No. 6,833,488 and PCT Published Patent Application No. WO2005/084724A1, both of which are hereby incorporated by reference in their entirety. The animals were sacrificed, their stomachs excised and the contents of the stomach were analyzed. No acute toxicity or change in behavior was noted in the animals following oral gavage of PMSF-1. Following sacrifice of the rats, no gross histopathalogy was observed in the rats' stomachs. The PMSF-1 device was observed in the stomachs of rats with an increased residence time noted for animals that were premedicated with H2 blockers or allowed to eat food following the device administration.

The primary objective of this study was to understand the residence time of PMSF-1 in the stomachs of rats following oral gavage of PMSF-1 in three different experimental conditions: 1) when animals do not eat food following intake of PMSF-1; 2) when animals are given H2 blockers which raises stomach pH prior to oral gavage of the polymer; and 3) when animals are allowed to eat food following oral gavage of the PMSF-1 polymer. A combination of visual inspection and quantification of stomach contents were used to reach conclusions. The animals which were pre-medicated with H2 blockers, clearly had a greater amount of PMSF-1 in their stomachs at the observed time points compared to animals which did not received H2 blockers. For instance, 90 minutes following oral gavage of the PMSF-1, 27% of the original PMSF-1 was recovered from the stomach of a rat pre-medicated with H2 blockers compared with no PMSF-1 being recovered at 90 minutes from a rat which received no H2 blockers. In addition, food which is documented to increase the pH of the stomach also caused the PMSF-1 to remain swollen for a greater period of time which is consistent with the results observed with H2 blockers.

The secondary objective of this study was to determine if oral gavage of the PMSF-1 materials produced any gross toxicology or obvious GI pathology. No acute toxicology was observed in the animals. In addition, fecal output and consistency was normal suggesting normal GI function. Gross histopathological examination of the stomach did not reveal any obvious abnormalities.

EXEMPLIFICATION

Example 1

Stomach Content Observation in Rats after the Administration of Polymeric Material Wistar rats with the characteristics listed in Table 1 were housed individually in Velaz T4 cages in conventional laboratory conditions. Room temperature was 20-24.degree. C. and the relative humidity was between 30-70%. Fluorescent lighting provided illumination approximately 12 hours per day. Feed and water containers were changed and sanitized at least once weekly. Lignocel (Velaz Ltd., Czech Republic) was used as bedding.

TABLE 1

| Wistar rats used in test system. | |
|---|---|
| Species & Strain | Wistar rat |
| Quality | conventional |
| Age on delivery | 6-9 weeks |
| Body weight at administration | 200-300 g |
| Number of groups | 3 |
| Rats per group | 2 |
| Total number of animals | 6 |

The animals were fed ad libium with standard pelletized rodent diet (NOE H4, Racio Breclav, Czech Republic) of monitored quality (analyzed minimally 2 times per year for possible toxic or microbiological contamination) during the acclimation and study periods. Water of monitored quality (analyzed minimally 2 times per year for possible toxic or microbiological contamination) was supplied ad libitum during the acclimation and study period. The rats were branded with picric acid solution and acclimated for 5 days.

The experimental design and group allocation are presented in Tables 2 and 3, respectively.

TABLE 2

Experimental design.

| Procedure | Date |
|---|---|
| Study initiation | Day 1 |
| Acclimation | 5 days |
| Initiation of experimental part | 30 days before |
| Health check | 31 days before |
| Start of the test tem administration | Day 1 |
| Dosing | single oral administration by gavage |
| Necropsy intervals | 30, 90 minutes |
| Body weight | Before administration |
| Proposed end of experimental part | Day 1 |

TABLE 3

Group allocation.

| Group # | Rats | Test Condition |
|---|---|---|
| 1 | F1, F2 | Premedicated with H2 blocker |
| 2 | F3, F4 | No premedication |
| 3 | F5, F6 | With food consumption |

All rats were fasted overnight. The first group of rats were premedicated with the H2 blocker PepcidAC®. (10 mg Famotidine, Johnson & Johnson-Merck Consumer Pharmaceuticals, 1 capsule/rat) 4 hours before administration. The second group was not premedicated and was not allowed access to food following oral gavage of PMSF-1. The third group was not premedicated, but was allowed access to food following oral gavage of PMSF-1.

The PMSF-1 powder was mixed with tap water at a ratio of 640 mg PMSF-1 to 50 mL water in order to swell the material. Rats were administered 5 mL of the swollen PMSF-1 by oral gavage. Rats in Group 3 (F5, F6) were given food which had been weighed immediately following oral gavage of PMSF-1 and were kept in the dark until necropsy. The food consumption of Group 3 was measured and recorded. Necropsy was performed according to Table 4.

TABLE 4

Necropsy intervals and stomach observation.

| Animal No. | H2 blocker premedication | Necropsy intervals (min) |
|---|---|---|
| F1 | Yes | 90 |
| F2 | Yes | 105 |
| F3 | No | 30 |
| F4 | No | 90 |
| F5 | No | 70 |
| F6 | No | 50 |

Rats were euthanized using ether, the animals' stomachs were excised and after the stomach outlets were tied off to prevent leakage, the stomachs were weighed. Next, the stomachs were cleaned and the stomach contents were weighed and visually inspected. Rats were observed for any signs of toxicity including vomiting, diarrhea, changes in activity and behavior after oral gavage of PMSF-1. Food consumption of Group 3 was recorded. Results for real time of PMSF-1 administration, necropsy period, and stomach contents examination are presented in Table 5.

TABLE 5

Stomach observation results.

| Animal number | H2 blocker | Administered PMSF-1 (ml) | Food consumed (g) | PMSF-1 + food (g) | Necropsy intervals (min.) | Stomach content (g)* | Remaining content (%) |
|---|---|---|---|---|---|---|---|
| F1 | + | 5.00 | 0.00 | 5.00 | 90 | 1.34 | 27% |
| F2 | + | 5.00 | 0.00 | 5.00 | 105 | 0.48 | 10% |
| F3 | − | 5.00 | 0.00 | 5.00 | 30 | 4.08 | 82% |
| F4 | − | 5.00 | 0.00 | 5.00 | 90 | 0.00 | 0% |
| F5 | − | 5.00 | 2.70 | 7.70 | 70 | 6.87 | 89% |
| F6 | − | 5.00 | 0.50 | 5.50 | 50 | 40.5 | 74% |

*F1-F4 only swollen PMSF-1 is included F5 and F6 include the mixture of PMSF-1 and food, as the two could not be separated The above results demonstrate that H2-blockers increase the total amount of time that PMSF-1 remains swollen in the stomachs of animals. Furthermore, food which is known to increase the pH of the stomach also caused the PMSF-1 to remain swollen for a greater period of time and the PMSF-1 mixed with the food. The results obtained with food therefore further shows that when taken in combination with PMSF-1, agents whether pharmacological or nutritional in nature, can improve the performance of PMSF-1 in the stomach environment.

We claim:

1. A method for inducing weight loss in a subject in need thereof, comprising (a) orally administering to the subject an appetite suppressing amount of a water-swellable polymer and a pH modifying agent which is a proton pump inhibitor and (b) administering to the subject an additional appetite suppressant or an antiobesity agent.

2. The method of claim 1, wherein the polymer is a superabsorbent polymer.

3. The method of claim 1, wherein the polymer is selected from the group consisting of homopolymers, copolymers, polymer blends, polymer composites, and combinations thereof.

4. The method of claim 1, wherein the proton pump inhibitor is selected from the group consisting of omeprazole, lansoprazole, esomeprazole, pantoprazole, abeprazole, and combinations thereof.

5. The method of claim 1, wherein the additional appetite suppressant or the antiobesity agent is selected from the group consisting of sibutramine hydrochloride, orlistat, rimonabant, benzphetamine, diethylproprion, mazindol phendimetrazine, phentermine, amphetamine, fenfluramine, nalmetrone or a combination thereof.

6. The method of claim 1, wherein the water swellable polymer is formulated as a tablet, a capsule, a shake, a syrup, a suspension, a powder or a bar.

7. The method of claim 1, wherein the pH modifying agent is administered simultaneously with the water-swellable polymer in the same dosage form.

8. The method of claim 1, wherein the pH modifying agent is administered simultaneously with the water-swellable polymer in a different dosage form.

9. The method of claim 1, wherein the pH modifying agent is administered before or after the administration of the water-swellable polymer.

10. The method of claim 1, further comprising administering to the subject a substance which causes the water-swellable polymer to degrade, disperse, and/or shrink.

11. The method of claim 10, wherein the substance which causes the water-swellable polymer to degrade, disperse, and/or shrink is an organic acid, an acidic drink or a protein.

12. The method of claim 11, wherein the protein is an enzyme selected from the group consisting of pepsin, pancreatin, and combinations thereof.

* * * * *